(12) United States Patent
Ruys et al.

(10) Patent No.: US 7,150,867 B2
(45) Date of Patent: Dec. 19, 2006

(54) RADIONUCLIDE-COATED PARTICULATE MATERIAL

(75) Inventors: Andrew John Ruys, Pymble (AU); Bruce Andrew Gray, Claremont (AU)

(73) Assignee: Sirtex Medical Limited, New South Wales (AU)

( * ) Notice: Subject to any disclaimer, the term of this patent is extended or adjusted under 35 U.S.C. 154(b) by 388 days.

(21) Appl. No.: 10/173,492

(22) Filed: Jun. 17, 2002

(65) Prior Publication Data

US 2002/0197207 A1 Dec. 26, 2002

Related U.S. Application Data

(63) Continuation of application No. PCT/AU01/01371, filed on Oct. 25, 2001.

(30) Foreign Application Priority Data

Oct. 25, 2000 (AU) .................................. PR0984

(51) Int. Cl.
*A61K 51/00* (2006.01)
*A61M 36/14* (2006.01)

(52) U.S. Cl. .................. 424/1.29; 424/1.11; 424/1.61; 424/1.37; 424/9.1

(58) Field of Classification Search ............... 424/1.11, 424/1.29, 1.33, 1.37, 1.65, 9.1, 9.32, 9.323, 424/9.36, 9.4, 9.42, 9.5, 9.51, 400, 450, 455, 424/458, 9.52, 1.61; 128/662.02, 660.01, 128/653.1

See application file for complete search history.

(56) References Cited

U.S. PATENT DOCUMENTS

| 4,108,975 | A | 8/1978 | Hales |
| 4,970,062 | A | 11/1990 | Atcher et al. |
| 5,362,473 | A | 11/1994 | Panek |
| 6,258,338 | B1 * | 7/2001 | Gray .................. 424/1.29 |
| 6,537,518 | B1 * | 3/2003 | Gray .................. 424/1.29 |

FOREIGN PATENT DOCUMENTS

| WO | 8603124 | 6/1986 |
| WO | 9519841 | 7/1995 |
| WO | 9951278 | 10/1999 |

OTHER PUBLICATIONS

Shepherd, F. et al., *Cancer*, vol. 70, No. 9, pp. 2250-2254 (Nov. 1, 1992).
Burton, M.A. et al., *Europ. J. Cancer Clin. Oncol.*, 24(8):1373-1376 (1988).
Meade, V. et al., *Europ. J. Cancer Clin. Oncol.*, 23:37-41 (1987).

* cited by examiner

*Primary Examiner*—Dameron L. Jones
(74) *Attorney, Agent, or Firm*—Merchant & Gould P.C.

(57) ABSTRACT

This invention relates to a particulate material comprising an inorganic low density, radiation tolerant core coated with a radionuclide, processes for its production and a method of radiation therapy utilizing the particulate material.

19 Claims, No Drawings

RADIONUCLIDE-COATED PARTICULATE MATERIAL

This application is a continuation of: International Application Number PCT/AU01/01371, filed Oct. 25, 2001.

FIELD OF THE INVENTION

This invention relates to a particulate material which comprises a radionuclide coated core, to a method for the production thereof, and to methods for the use of this particulate material.

In one aspect of this invention, there is provided a low-density particulate material which may be in the form of microspheres which are designed to be administered into the arterial blood supply of an organ to be treated, whereby the microspheres become entrapped in the small blood vessels of the target organ and irradiate it. The size and shape of the microspheres may be designed in order to facilitate transport of the material into the target organ by blood flow.

In another aspect of this invention, there are provided larger sized particles in the form of wires or seeds (collectively referred to herein as seeds) that can be directly implanted into tissues. These particles may be designed for implantation into malignant tumours, of which tumours of the prostate, lung, liver are some examples.

The present invention therefore has utility in the treatment of various forms of cancer and tumours, but particularly in the treatment of primary and secondary cancer of the liver and the brain.

BACKGROUND OF THE INVENTION

Many previous attempts have been made to locally administer radioactive materials to patients with cancer, as a form of therapy. In some of these, the radioactive materials have been incorporated into small particles, seeds, wires and similar related configurations that can be directly implanted into the cancer. When radioactive particles are administered into the blood supply of the target organ, the technique has become known as Selective Internal Radiation Therapy (SIRT). Generally, the main form of application of SIRT has been its use to treat cancers in the liver.

There are many potential advantages of SIRT over conventional, external beam radiotherapy. Firstly, the radiation is delivered preferentially to the cancer within the target organ. Secondly, the radiation is slowly and continually delivered as the radionuclide decays. Thirdly, by manipulating the arterial blood supply with vasoactive substances (such as Angiotensin-2), it is possible to enhance the percentage of radioactive particles that go to the cancerous part of the organ, as opposed to the healthy normal tissues. This has the effect of preferentially increasing the radiation dose to the cancer while maintaining the radiation dose to the normal tissues at a lower level (Burton, M. A. et al.; Effect of Angiotensin-2 on blood flow in the transplanted sheep squamous cell carcinoma. Europ. J. Cancer Clin. Oncol. 1988, 24(8): 1373–1376).

When microspheres or other small particles are administered into the arterial blood supply of a target organ, it is desirable to have them of a size, shape and density that results in the optimal homogeneous distribution within the target organ. If the microspheres or small particles do not distribute evenly, and as a function of the absolute arterial blood flow, then they may accumulate in excessive numbers in some areas and cause focal areas of excessive radiation. It has been shown that microspheres of approximately 25–50 micron in diameter have the best distribution characteristics when administered into the arterial circulation of the liver (Meade, V. et al.; Distribution of different sized microspheres in experimental hepatic tumours. Europ. J. Cancer & Clin. Oncol. 1987, 23:23–41).

If the microspheres or seeds do not contain sufficient ionising radiation, then an excessive number will be required to deliver the required radiation dose to the target organ. It has been shown that if large numbers of microspheres are administered into the arterial supply of the liver, then they accumulate in and block the small arteries leading to the tumour, rather than distribute evenly in the capillaries and precapillary arterioles of the tumour. Therefore, it is desirable to use the minimum number of microspheres that will provide an even distribution in the vascular network of the tumour circulation.

For radioactive microspheres to be used successfully for the treatment of cancer, the radiation emitted from the microspheres should be of high energy and short range. This ensures that the energy emitted from the microspheres will be deposited into the tissues immediately around the microspheres and not into tissues that are not the target of the radiation treatment. There are many radionuclides that can be incorporated into microspheres that can be used for SIRT. In this treatment mode, it is desirable to use microspheres or seeds that emit high energy but short penetration beta radiation that will confine the radiation effects to the immediate vicinity of the microspheres or seeds.

If the microspheres or seeds contain other radioactive substances that are not required for the radiation treatment of the target tissue or for dosimetry or imaging, then unwanted and deleterious radiation effects may occur. It is therefore desirable to have microspheres or seeds of such a composition that they primarily only contain the desired radionuclide(s).

In the earliest clinical use of yttrium-90-containing microspheres, the yttrium was incorporated into a polymeric matrix that was formulated into microspheres. While these microspheres were of an appropriate size to ensure good distribution characteristics in the liver, there were several instances in which the yttrium-90 leached from the microspheres and caused inappropriate radiation of other tissues. The other disadvantage of resin based microspheres is that production requires loading of the microspheres after the radionuclide has been formed and this results in radiation exposure to manufacturing staff. There is always the potential for these microspheres to leach the yttium-90 and the amount of yttrium-90 that can be loaded onto the resin is also limited.

In one attempt to overcome the problem of leaching, a radioactive microsphere comprising a biologically compatible glass material containing a beta or gamma radiation emitting radioisotope such as yttrium-90 distributed homogeneously throughout the glass as one of the glass component oxides, has been developed (International Patent Publication No. WO 86/03124). These microspheres are solid glass and contain the element yttrium-89 as a component of the glass, which can be activated to the radionuclide yttrium-90 by placing the microspheres in a neutron beam. These glass microspheres have several disadvantages including being of a higher density than is desirable, containing the yttrium-90 within the matrix of the microspheres as opposed to on the surface and also containing significant amounts of other elements such as glass modifier oxides and fluxing oxides which are activated to undesirable radionuclides when placed in a neutron beam, and requiring large numbers of microspheres in order to deliver the required amount of radiation to the target tissue.

There have been several reports of clinical studies on the use of solid glass radioactive microspheres. In one report, ten patients with primary hepatocellular carcinoma were treated, however no patient had a complete or partial response (Shepherd, F. et al., Cancer, Nov. 1, 1992, Vol.70, No.9, pp 2250–2254).

Another approach has been focussed on the use of small hollow or cup-shaped ceramic particles or microspheres, wherein the ceramic base material consists or comprises yttria or the like (see International Patent Application No. PCT/AU95/00027; WO 95/19841).

SUMMARY OF THE INVENTION

In one aspect the present invention provides a particulate material comprising an inorganic low density, radiation-tolerant core coated with a radionuclide.

In another aspect, the present invention provides a process for the production of an particulate material comprising forming a coating of radionuclide on an inorganic low density, radiation-tolerant core.

In one embodiment, the coating of radionuclide may be formed by applying a coating of radionuclide precursor and then activating the precursor to form the radionuclide. Alternatively, the radionuclide may be coated directly onto the core.

The present invention also provides a method of radiation therapy of a patient which comprises administration to the patient of a particulate material comprising an inorganic low density, radiation-tolerant core coated with a radionuclide.

The present invention also provides for the use of a particulate material comprising an inorganic low density, radiation-tolerant core coated with a radionuclide in radiation therapy of a patient.

DETAILED DESCRIPTION

As referred to herein, the term "radiation tolerant" refers to the ability of a material to be irradiated, particularly neutron irradiated, without physical degradation or subsequent emission of radiation of an undesirable nature. Some organic materials will undergo physical degradation upon exposure to a neutron beam, and such degradation will preclude the safe use in SIRT therapy. The core therefore comprises inorganic materials, such as ceramics, glasses and metals, since radiation tolerance can be found in these inorganic materials. Preferably the core is a non-porous glass. By glass is meant an inorganic amorphous material. By ceramic is meant an inorganic crystalline non-metallic material. This definition also includes glass ceramics.

Preferably the core does not contain more than 10% by weight of any compound that is not radiation tolerant. More preferably the core does not contain more than 10% of any compound other than $SiO_2$ Most preferably, the core is at least 75%, 80%, 90%, 95%, 98%, 99% or 100% $SiO_2$. Such a core material provides a low density core to which the desired coating can be applied or a surface coating. The thickness of the coating can be varied to allow the production of particles having a range of specific activities depending on the thickness of the coating.

As referred to herein low density is a relative term. The suitable density will depend on the thickness of coating and radionuclide. The density of the core is preferably less than 2.5 g/cc, more preferably less than 2.4, 2.3 or 2.2 g/cc. The specific gravity of the coated core is preferably less than 2.5 g/cc, more preferably less than 2.3 g/cc.

Radionuclides suitable for this invention include but are not restricted to holmium, iodine, phosphorus, rhenium, and samarium. Other radionuclides with suitable characteristics can also be used. Preferably the radionuclide will have a half life in the range of from 5 to 1000 hours.

Of particular suitability for use in this form of treatment are the unstable isotopes of yttrium (Y-90). Yttrium-90 is the unstable isotope of yttrium-89 which can be manufactured by placing the stable yttrium-89 in a neutron beam. The yttrium-90 that is generated decays with a half life of 64 hours, while emitting a high energy pure beta radiation.

The preferred radionuclide yttrium is preferably provided in the form of yttrium oxide. Yttria is a dense ceramic (5.0 g/cc). However, by forming a thin surface coating on the core, the amount of heavy radionuclide is small, the contribution to the specific gravity of the particulate material is small, but the radioactive emission capability is at a maximum since the radionuclide is not distributed throughout the particle, but concentrated on an outer layer. The radionuclide layer may not be the outermost layer, there may be other coatings on the core. Such other coatings may serve to protect the radionuclide layer or core material.

The radionuclide may be deposited onto the core using finely-divided solid radionuclide material, such as a yttria colloidal sol. Adhesion in this case will be via electrostatic forces such as heterocoagulation, followed by permanent fixation by solid state diffusion via heat-treatment methods. The radionuclide may also be deposited onto the core using a gas-entrained radionuclide precursor, for example an aerosol utilising an electrostatic attachment mechanism, or a radionuclide precursor vapor such as a sputter-coating process, chemical vapour deposition process, or physical vapor deposition process. Further, the radionuclide may be deposited onto the glass microsphere or seed using a radionuclide precursor solution, for example a solution of radionuclide salt, or a solution of radionuclide alkoxide or other radionuclide organometallic. Adhesion in this case would be via precipitation of an insoluble film which may or may not be subjected to a post-coating heat-treatment procedure for the purposes of enhancing fixation. Where a radionuclide precursor is deposited as a coating on the core, the precursor is subsequently activated, for example, by irradiation in a neutron beam.

Preferably the method of coating is sputter coating. Sputter coating is known for coating large metal objects to prevent corrosion. Incorporated herein by reference is "Engineering coatings: Design and Application by Stan Grainger and Jane Blunt", $2^{nd}$ edition, Abington Publishing, Cambridge UK, which describes methods of vapour deposition sputter coating, chemical vapour deposition and other coating methods. In a particularly preferred embodiment, the sputter coating is applied to cores which are placed on a vibrating table. Preferably the table is vibrating at a frequency of between 10 and 500 Hz, more preferably the frequency is between 50 and 100 Hz. The amplitude is preferably in the range of from 0.01 mm to 1.0 mm and more preferably in the range of from 0.1 mm to 0.2 mm The cores placed on the table are preferably not placed in a deep pile, the depth should be such that the particles are all exposed to the vapour bombardment at some stage during the bombardment process.

The coating size may be varied depending on the dose to be administered to the patient. Preferably the coating is in the range of from 1 to 1000 nm, more preferably it is less than 500 nm, more preferably less than 100 nm, and even more preferably less than 10nm. For example, using a $SiO_2$ core of 2.15 g/cc and a coating of 45 nm of yttrium oxide (to a volume of 0.85%), the density of the coated core will be 2.17 g/cc. Using a $SiO_2$ core of 2.15 g/cc and a coating of 450 nm of yttrium oxide (to a volume of 8.68%), the density of the coated core will be 2.4 g/cc. It is not necessary that the coating is even, the irradiation of the tumour will be effective if the coating is uneven. It would be desirable to have microspheres in which the radionuclide was concentrated in appropriate amounts on the outside or outer layers of the particulate material as this would provide a higher amount of the radionuclide and hence a lesser number of microspheres can be used to treat the patient. High concentrations of the radionuclide could be added by increasing the thickness of the coating. Also it would allow closer contact between the radioactive emission and the target tissue. Also these microspheres could be manufactured to contain a precise amount of required radionuclide and activation of the microspheres can occur after the microsphere had been fully manufactured.

The coated cores may be of a size suitable for SIRT therapy, i.e., a diameter in the range of from 5 to 200 microns, preferably 15 to 100 microns, more preferably from 20 to 50 microns and more particularly in the range of from 30 to 35 microns. Alternatively they be of a size suitable for implanting directly in a tumour or other tissue. Coated seeds of a size suitable for direct implantation into tissues are in the size range of from 100 microns to 5 centimetres.

It is preferable that the microspheres or seeds be stable so that material does not leach from the microspheres when administered into the body of a human or other mammalian patient and cause the patient harm. As used herein, references to the radionuclide being stably incorporated are to be understood as referring to incorporation of the radionuclide so that it does not leach out of, or spall from, the coating under physiological conditions, such as in storage or in the patient. Accordingly, the radionuclide coating on the core should remain adherent to the core under these conditions.

In another application of this invention it is possible to include materials that will have secondary or tertiary radioactive emissions if it is desired that these secondary or tertiary emissions can be used for other purposes, such as for radiation dosimetry or external imaging of the particulate material. It is possible to incorporate such other material into an additional coating or the same coating as the first radionuclide. Alternatively, the other material may be included in the core. When the microsphere or seed is then activated by placing it into a neutron beam, the primary radionuclide is activated to produce the desired therapeutic radiation, and the secondary or tertiary radionuclide is activated to produce the secondary or tertiary emission that can be used for dosimetry or imaging. If other radionuclides that emit gamma emissions are also incorporated into the microspheres, then external dosimetry and localisation on a gamma camera can occur, thereby greatly increasing the utility of the particulate material.

In a preferred embodiment, the process for production of the particulate material of the present invention is carried out by firstly producing a frit of the glass, sieving the frit into appropriate size ranges, and flame-spheroidising the frit to produce glass microspheres. The microspherical core is then coated with the required radionuclide precursor, such as yttria either from solution or by direct application, for example by sputter coating. Finally, the radionuclide precursor-coated microspheres are irradiated in a neutron beam to activate the microspheres.

The present invention also provides a method of radiation therapy of a human or other mammalian patient, which comprises administration to the patient of a particulate material as described above.

In yet another aspect, this invention also extends to the use of a particulate material as described above in radiation therapy of a human or other mammalian patient.

Throughout this specification, unless the context requires otherwise, the word "comprise", and or variations such as "comprises" or "comprising", will be understood to imply the inclusion of a stated integer or step or group of integers or steps but not the exclusion of any other integer or step or group of integers or steps.

Further features of the present invention are more fully described in the following Examples. It is to-be understood, however, that this detailed description is included solely for the purposes of exemplifying the present invention, and should not be understood in any way as a restriction on the broad description of the invention as set out above.

EXAMPLE 1

High-purity oxide components are batched in accordance with the following glass composition given in percentages by weight: 72% $SiO_2$, 25% $B_2O_3$, 1% $Al_2O_3$, 0.5% $Li_2O$, 0.5% Na $K_2O$. The mixture of parent oxides is smelted in a contamination-free crucible, homogenised, and then quenched in demineralised water to produce the frit. The frit is then ground and sieved to yield a 20 to 50 micron size range fraction. This sieved frit is then flame spheroidised by passing the powder from a feed hopper through a flame torch. The resultant product is sieved into the 30 to 35 micron size range fraction.

A 1 wt % suspension of the microspheres in alcohol is prepared and placed in a beaker on a magnetic stirrer inside a glove box. Yttrium alkoxide is added at an amount necessary to produce a 45 nm thick surface coating, i.e., an amount such that the yttria yield from the yttrium alkoxide is 2.4 wt % of the weight of microspheres. After a period of mixing, the yttrium alkoxide is hydrolised. The microspheres are then rinsed with three repeats, then dried. The coated microspheres are then irradiated in a neutron beam, sterilised, and packed in a sterile tube.

EXAMPLE 2

Solid (not hollow) microspheres of high-purity amorphous silica (also known as fused silica) with an average diameter of 30 microns, and a standard deviation of 15 microns, are placed onto a vibrating platen. This vibrating platen is located inside a sputter-coating machine, oriented parallel to the sputter target, and centred on the same longitudinal axis as that of the sputter target. The sputter target comprises a disk of high-purity yttrium oxide (99.9999% pure), 100 mm in diameter, and is located 70 mm above the platen. The platen is made of aluminium, it is a 100 mm diameter disk with a peripheral wall 10 mm high.

Approximately 5 grams of microspheres are placed in the vibrating platen "dish", as a thin layer of microspheres about 0.5 mm deep. The sputter coater is then sealed and evacuated to a vacuum of about $10^{-4}$ mbar. At this point, the vibration of the platen is switched on, the frequency of the vibration is about 50 Hz and the amplitude is about 0.1 mm. Coating then takes place by RF plasma coating using argon as the ionization gas. The coating thickness is approximately 100 nm. This corresponds to particles comprising approximately 4 weight % of yttria as a surface coating and approximately 96 weight % silica as the microsphere core.

The sputter coater is then opened and the particles are removed from the platen. They are then subsequently irradiated under a high neutron flux such that their beta irradiation level corresponds to about 5 GBq/gram.

EXAMPLE 3

The technique of Selective Internal Radiation Therapy (SIRT) has been described above. It involves either a laparotomy to expose the hepatic arterial circulation or the insertion of a catheter into the hepatic artery via the femoral, brachial or other suitable artery. This may be followed by the infusion of Angiotensin-2 into the hepatic artery to redirect arterial blood to flow into the metastatic tumour component of the liver and away from the normal parenchyma. This is followed by embolisation of yttrium-90 coated microspheres (produced in accordance with Example 1 or Example 2) into the arterial circulation so that they become lodged in the microcirculation of the tumour. Repeated injections of microspheres are made until the desired radiation level in the normal liver parenchyma is reached. By way of example, an amount of yttrium-90 activity that will result in an inferred radiation dose to the normal liver of approximately 80 Gy may be delivered. Because the radiation from SIRT is delivered as a series of discrete point sources, the dose of 80 Gy is an average dose with many normal liver parenchymal cells receiving much less than that dose.

The measurement of tumour response by objective parameters including reduction in tumour volume and serial estimations of serum carcino-embryonic antigen (CEA) levels, is an acceptable index of the ability of the treatment to alter the biological behaviour of the tumour.

The invention claimed is:

1. A method of manufacturing a particulate material comprising a radionuclide coated inorganic, low density core, wherein said method comprises the steps of: coating a radionuclide onto said core by the process of sputter coating, characterized in that the sputter coating process is carried out on a vibrating table.

2. The method according to claim 1, wherein the frequency and amplitude of a vibration of the table are respectively about 10 to 500 Hz and between about 0.01 mm to 1.0 mm.

3. The method according to claim 1, wherein the particulate material comprises a wire or seed in the size range of from 100 microns to 200 centimeters.

4. The method according to claim 1, wherein the inorganic core comprises at least 75% $SiO_2$.

5. The method according to claim 1, wherein the radionuclide is yttrium-90.

6. The method according to claim 1, wherein the density of the inorganic core is less than 2.5 g/cc.

7. A particulate material comprising a radionuclide coated inorganic low density core produced by the method of claim 1.

8. The particulate material according to claim 7, wherein the inorganic core comprises a microsphere having a diameter in the range of from 5 to 200 microns.

9. The particulate material according to claim 7, wherein the inorganic core comprises a wire or seed in the size range of from 100 microns to 5 centimeters.

10. The particulate material of claim 7, wherein the inorganic core comprises at least 75% $SiO_2$.

11. The particulate material of claim 7, wherein the inorganic core comprises at least 90%, $SiO_2$.

12. The particulate material of claim 7, wherein the density of the inorganic core is less than 2.5 g/cc.

13. A method of radiation therapy comprising administering to a patient a particulate material comprising the radionuclide coated inorganic low density core of claim 7.

14. The method according to claim 13, wherein the radionuclide is yttrium-90.

15. A method according to claim 13, wherein the radiation therapy comprises treatment of a primary or secondary liver cancer.

16. The particulate material according to claim 7, wherein the radionuclide is yttrium-90.

17. The method according to claim 1, wherein the density of the inorganic core is less than 2.2 g/cc.

18. The particulate material of claim 7, wherein the inorganic core comprises at least 95% $SiO_2$.

19. The particulate material of claim 7, wherein the density of the inorganic core is less than 2.2 g/cc.

* * * * *

UNITED STATES PATENT AND TRADEMARK OFFICE
CERTIFICATE OF CORRECTION

| | | |
|---|---|---|
| PATENT NO. | : 7,150,867 B2 | Page 1 of 1 |
| APPLICATION NO. | : 10/173492 | |
| DATED | : December 19, 2006 | |
| INVENTOR(S) | : Andrew John Ruys and Bruce Nathaniel Gray | |

It is certified that error appears in the above-identified patent and that said Letters Patent is hereby corrected as shown below:

On the title page 75 replace "Bruce <u>Andrew</u> Gray."

With --Bruce <u>Nathaniel</u> Gray.--

Signed and Sealed this

Tenth Day of April, 2007

JON W. DUDAS
*Director of the United States Patent and Trademark Office*